(12) United States Patent
Weener et al.

(10) Patent No.: US 11,994,515 B2
(45) Date of Patent: May 28, 2024

(54) METHOD OF PERFORMING AN ASSAY

(71) Applicant: Minq Solutions B.V., Deventer (NL)

(72) Inventors: Jan Willem Weener, Deventer (NL); Edin Sarajlic, Zutphen (NL)

(73) Assignee: Minq Solutions B.V., Deventer (NL)

( * ) Notice: Subject to any disclaimer, the term of this patent is extended or adjusted under 35 U.S.C. 154(b) by 914 days.

(21) Appl. No.: 16/467,661

(22) PCT Filed: Dec. 1, 2017

(86) PCT No.: PCT/NL2017/050804
§ 371 (c)(1),
(2) Date: Jun. 7, 2019

(87) PCT Pub. No.: WO2018/111096
PCT Pub. Date: Jun. 21, 2018

(65) Prior Publication Data
US 2019/0369090 A1 Dec. 5, 2019

(30) Foreign Application Priority Data

Dec. 12, 2016 (NL) .................................... 2017979
Dec. 12, 2016 (NL) .................................... 2017982

(51) Int. Cl.
G01N 33/53 (2006.01)
B01L 3/00 (2006.01)
(Continued)

(52) U.S. Cl.
CPC ........ *G01N 33/5304* (2013.01); *B01L 3/5085* (2013.01); *C12M 23/12* (2013.01);
(Continued)

(58) Field of Classification Search
CPC .................. D21H 19/385; D21H 21/34; B01J 2219/00317; B01J 2219/00722;
(Continued)

(56) References Cited

U.S. PATENT DOCUMENTS

2003/0215941 A1   11/2003   Campbell et al.
2012/0107925 A1*   5/2012   Li .......................... B01D 69/02
                                                           435/325
(Continued)

FOREIGN PATENT DOCUMENTS

GB   2401942 A        11/2004
WO   2011011350 A2    1/2011
WO   2013180567 A2    12/2013

OTHER PUBLICATIONS

Fan et al "Combinatorial labeling of single cells for gene expression cytometry". Science. Feb. 6, 2015;347(6222): 1258367. doi: 10.1126/science.1258367. PMID: 25657253. (Year: 2015).*

*Primary Examiner* — Christine T Mui
*Assistant Examiner* — Jonathan Bortoli
(74) *Attorney, Agent, or Firm* — Shewchuk IP Services, LLC; Jeffrey D. Shewchuk

(57) ABSTRACT

The invention relates to a method of performing an assay for a compound. The method makes use of a device (390) which has a plurality of wells (340) which contain cells, and according to the method a liquid is transferred from the wells (340) to a substrate which is used to perform the assay. Each well (340) of the device comprises a bottom provided with a through-hole (370) extending from the well (340) to the backside of the device (390). Liquid containing the compound is transferred via the through-holes (370) to the substrate.

16 Claims, 10 Drawing Sheets

Figure 1:
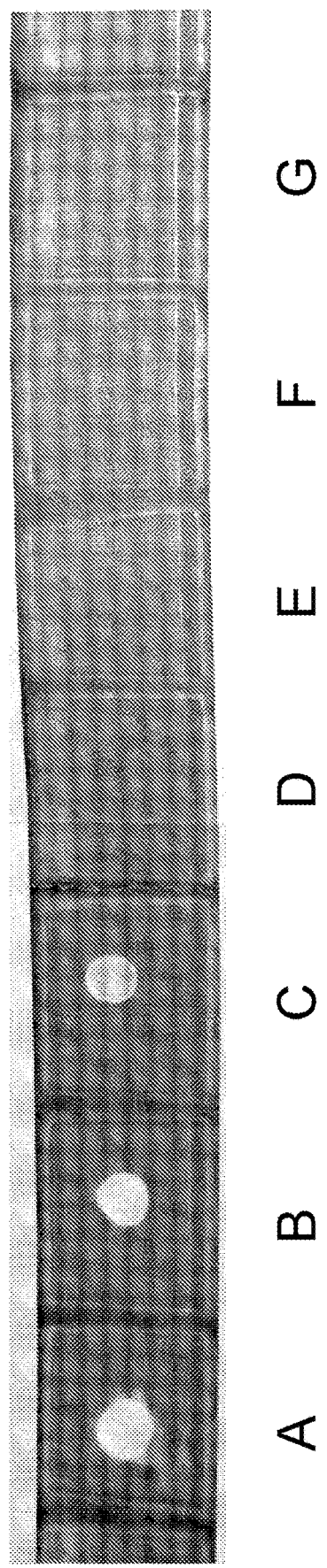

(51) Int. Cl.
  *C12M 1/32* (2006.01)
  *G01N 33/50* (2006.01)
(52) U.S. Cl.
  CPC .. *G01N 33/5008* (2013.01); *B01L 2200/0647* (2013.01); *B01L 2300/0829* (2013.01); *B01L 2300/0851* (2013.01)
(58) Field of Classification Search
  CPC .... B01J 2219/00743; B01L 2200/0647; B01L 2300/0829; B01L 2300/0851; B01L 3/5085; C12M 23/12; C12Q 1/686; G01N 33/5008; G01N 33/5304
  See application file for complete search history.

(56) References Cited

U.S. PATENT DOCUMENTS

| | | | | |
|---|---|---|---|---|
| 2012/0328488 | A1* | 12/2012 | Puntambekar | B01L 3/5025 422/503 |
| 2013/0190212 | A1* | 7/2013 | Handique | G01N 15/1436 506/40 |
| 2015/0025347 | A1* | 1/2015 | Song | G01N 33/54306 600/362 |

\* cited by examiner

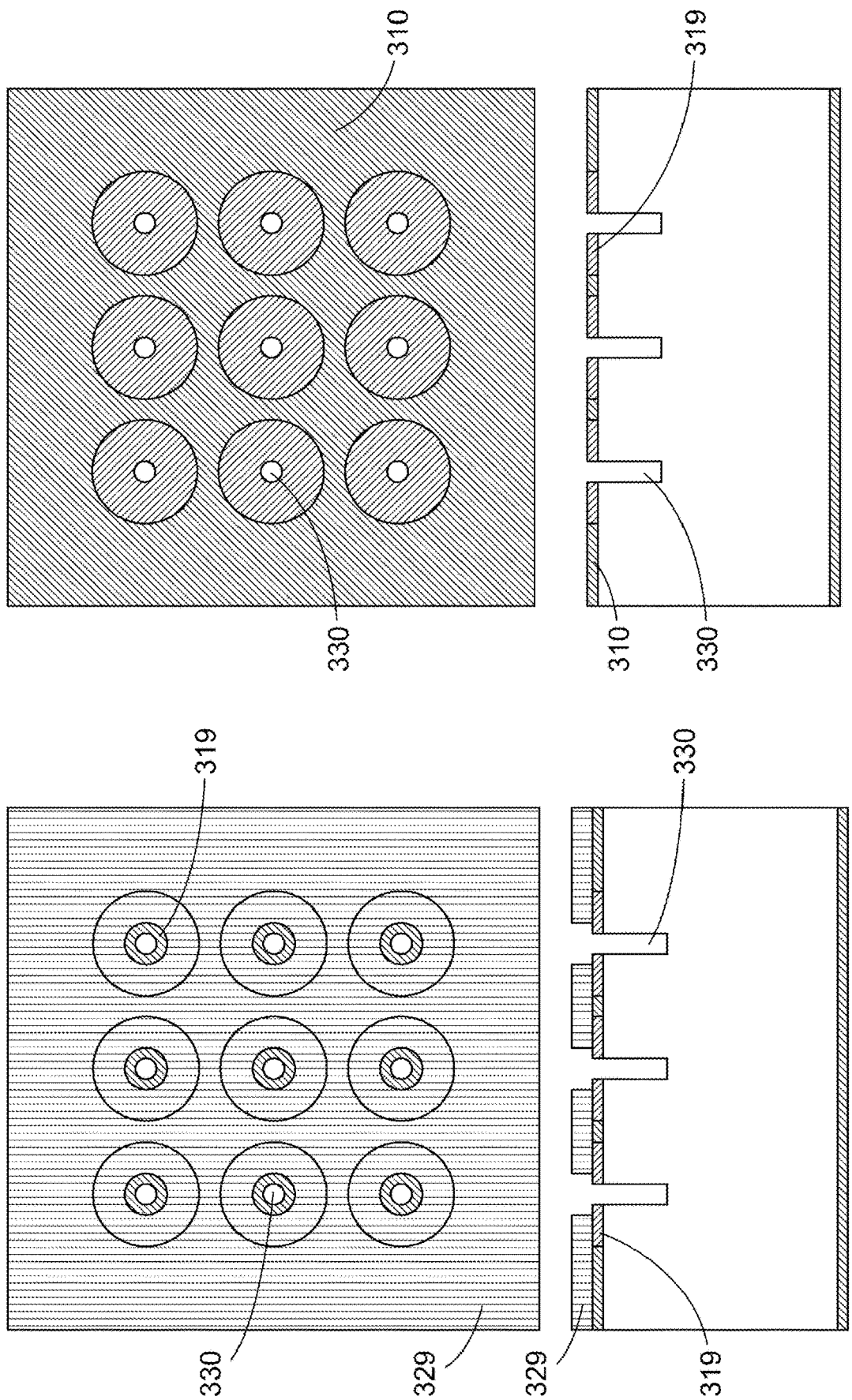

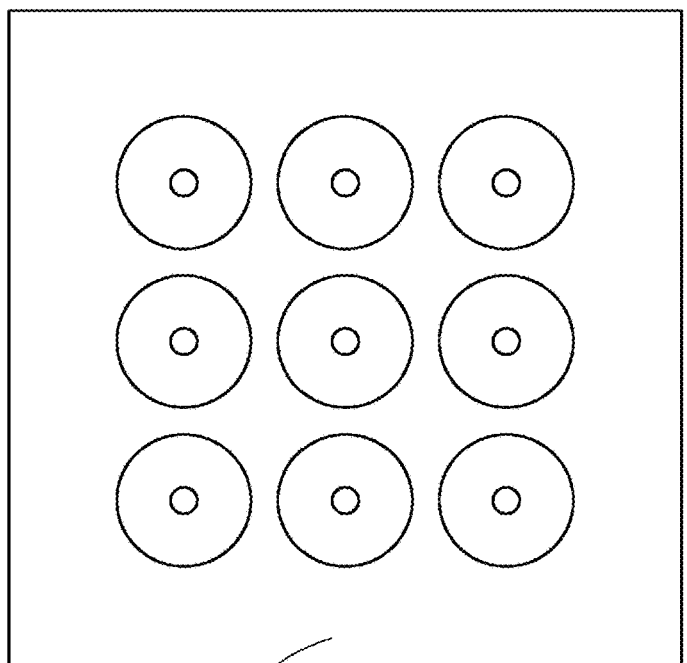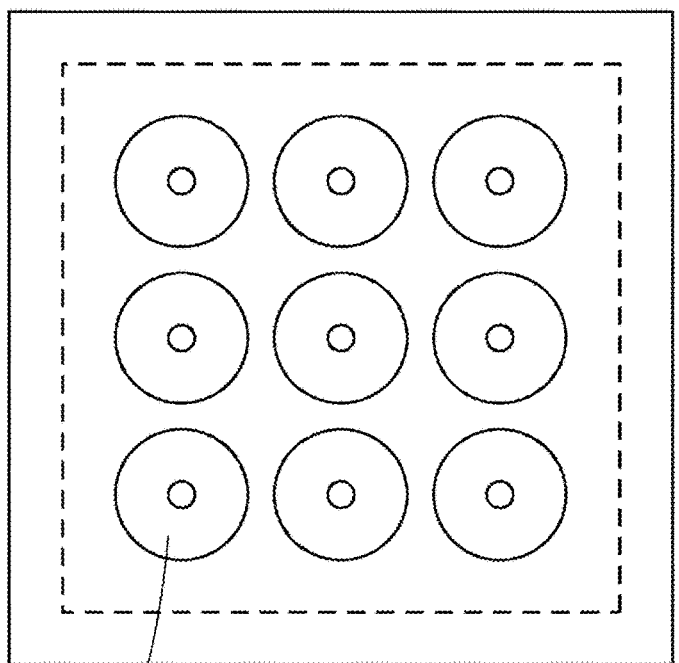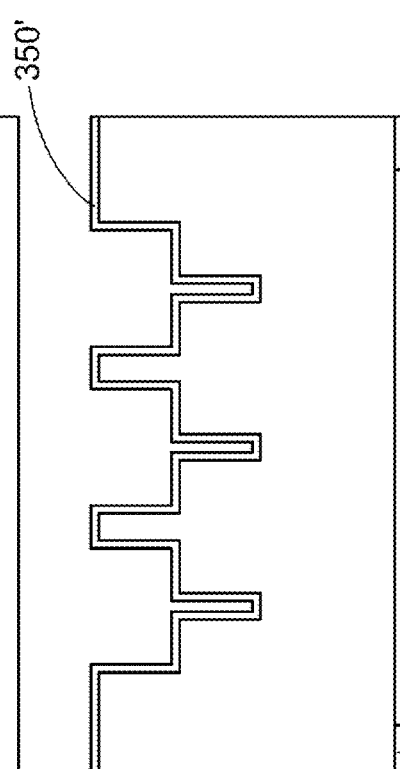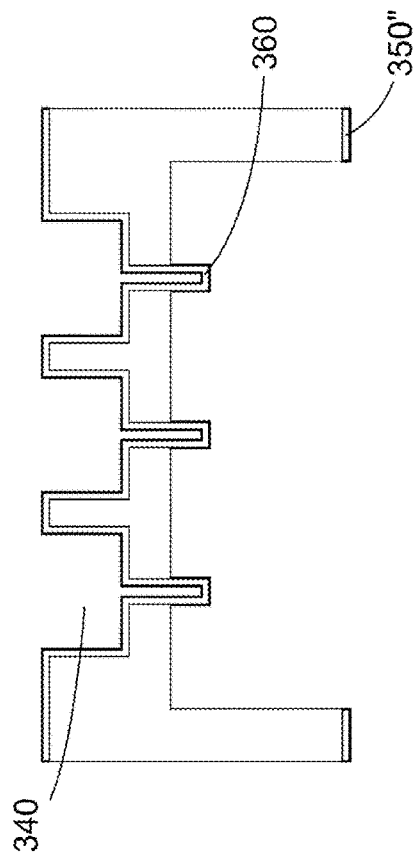
Fig. 3M
Fig. 3N

METHOD OF PERFORMING AN ASSAY

The present invention relates to a method of performing an assay for a compound using a device, wherein the device comprises
  a frontside with a plurality of wells, and
  a backside;
the plurality of wells of the device contains cells;
said method comprising the steps of
  transferring liquid from the wells to the substrate, and
  using the substrate to perform the assay.

A method of performing an assay is disclosed by Christopher Love in "A microengraving method for rapid selection of single cells producing antigen-specific antibodies" (Nature Biotechnology, 2006, vol. 24(6) p. 703). In this method an assay is performed using a device comprising a plurality of wells, wherein the content (supernatant) of all the wells is transferred simultaneously to a substrate (glass plate), which substrate is used for the assay.

It is an object of the present invention to provide an alternative method according to the preamble.

To this end, a method according to the preamble is characterized in that each well of the plurality of wells comprises a bottom provided with a through-hole extending from the well to the backside of the device;
wherein the method comprises the steps of
  contacting the backside of the device with the substrate,
  performing the step of transferring liquid from the wells to the substrate by transferring liquid from the wells via the through-holes to the substrate, and
  performing the step of performing the assay using the substrate.

It has been found that the method allows for the convenient detection of the compound. It is not necessary to hold the device upside down. The device is for example a MEMS array. The through-hole allows for transfer of liquid containing the compound to a spot of relatively small size, in particular smaller than the surface area of the well in the main plane of the device.

The compound is advantageously a compound excreted by a cell.

The compound is typically an organic compound, such as a metabolite, or a protein.

Typically, an assay will involve the addition of a reagent, such as a labelled antibody or labelled antigen.

The substrate will typically have a planar side for contacting the backside of the device, and in general will be a planar substrate, such as a sheet of material. It will be held in contact with the backside of the device to pass compound from the well to the substrate. As liquid is transferred from the multitude of wells to the substrate, this substrate comprises a corresponding multitude of areas contacted with liquid from the device. Typically the substrate will be taken away (separated from the device) to perform the assay. This allows the cells to be kept under conditions suitable for keeping them alive and/or reduced the risk of contamination of the cells and/or avoid contact of the cells with any reagents for the assay.

While the assay may be of any type, including a radioactive tracer-based assay, it is convenient if the assay is some type of optical assay, such as a chemiluminescence-based assay, a fluorescence-based assay or enzyme-based assay where the enzyme effects a change in color (or fluorescence).

Typically the compound transferred through the through-holes will be adsorbed on the substrate, using specific absorption or a-specific adsorption as desired.

It has been found that the method according to the invention can be performed with relatively little manual labor.

It has also been found that the assay can be performed in little time, such as in 2 hours or less.

According to a favourable embodiment, the compound is excreted by the cells in the device, following which the step of performing the assay using the substrate is performed.

This is an important application of the method, with a variety of applications, for example selecting high-producing hybridoma cells.

It has been found that the method allows for the convenient detection of the compound. The risk that a cell is dislodged from the well is reduced as it is not necessary to hold the device upside down. The device is for example a MEMS array, as it allows for a great number of wells (thousands or even millions). The through-hole is typically not capable of letting the cell pass through the through-hole, and thus will typically be of smaller dimensions than the cells in the plurality of wells.

At least a part of the plurality of wells contains at least one cell. The cells are typically eukaryotic cells, such as a mammalian cell. It may be an immortal cell (which term includes an immortalised cell), or non-immortal cell.

The liquid comprising the compound excreted by a cell is commonly referred to as supernatant. In the method according to the invention, the liquid flowing from the well passes the cell, which is hence in contact with medium during this step of the procedure and thus isn't cut off from medium during this step. It is conceivable that there is a layer of fresh medium on top of the device during this step.

Incubation of the cells in the wells of the device may be done for, for example, at least 1 minute or for longer periods such as at least one hour or at least 24 hours, as desired or needed for the particular objective of the assay and the compound to be detected using the assay.

The cells are arranged in the device.

According to a favourable embodiment, at least 10% of the plurality of wells contain a single cell.

Thus it is possible to screen a large number of cells and determine their individual characteristic with respect to the compound measured using the assay. It is known in the art to prepare an array of wells with the wells containing a single cell, for example from EP2855020. The inventor has realised that the restricted flow of liquid through the through-hole can still be used for an assay. In contrast to the method according of Love, the risk that the cell in a well is transferred to the substrate and is lost is reduced, as the device does not need to be held upside down, and also the risk of cross-contamination can be reduced as the closest distance between supernatants from two adjacent wells transferred to the substrate is greater. In addition, the risk of the cell contacting a reagent involved in the assay is reduced.

According to a favourable embodiment, the through-hole has dimensions that do not allow the cell to pass through the through-hole.

Thus the cell is physically retained in the well, allowing it to be available for further use, such as for a further assay. It also ensures that the cell does not contact the substrate.

The cell is kept physically separated from the substrate.

Generally speaking for a device according to the invention suitable for performing an assay on an eukaryotic cell, typical dimensions of the through-hole are 5 μm or smaller in at least one dimension parallel to the backside of the device and preferably less than 3 μm. Preferably these values go for both dimensions parallel to the backside of the device.

According to a favourable embodiment, the assay is an immunoassay.

An immunoassay allows a great variety of compounds to be detected. The immunuoassay may be of any type, such as a sandwich assay. It has been found that the method according to the present invention is capable of determining proteins such as antibodies in an amount of less than 1 ng.

According to an especially preferred embodiment, the substrate comprises a micro-porous substrate.

More liquid from the wells can be introduced, allowing a greater sensitivity. It also allows for the compound to be absorbed in a volume that is relatively compact, enhancing the sensitivity even more. Furthermore, the average diffusion distance is small, allowing the method according to the present invention to be relatively quick. According to a preferred embodiment, the substrate allows for a greater rate of transport of liquid in a direction transverse to the main plane of the substrate than in a direction parallel to the main plane. This helps to avoid cross-contamination and to keep the compound from a particular well with in more localised area of the substrate. In contrast, the method of Love would not allow for the use of micro-porous substrate as the adjacent supernatants would contact each other and/or cells would be devoid of medium during the overnight incubation.

The substrate is for example glassfiber, paper, or nitrocellulose.

Typically, the pores of the micro-porous substrate will be between 0.05 μm and 10 μm, preferably between 0.2 μm and 2 μm.

According to a favourable embodiment, the liquid is transferred using a pressure difference with a relatively low pressure at a side of the substrate opposite of the device.

The pressure may for example be achieved by increasing the air pressure at the front side of the device. In addition or alternatively, suction may be applied in any suitable manner, e.g. using reduced pressure ("vacuum") at the backside of the substrate or by using an absorbing pad in contact with the backside of substrate.

According to a favourable embodiment, the substrate is a polymer, preferably a polymer chosen from i) polyvinylidene difluoride, and ii) nitrocellulose.

These substrates are very well suited for assays, in particular optical assays and immunoassays. Currently polyvinylidene difluoride is most preferred. It is in particular preferred that the polymer substrate is a micro-porous polymer.

According to a favourable embodiment, the device comprises a frontside with the plurality of wells and a backside, the backside comprising a plurality of protruding capillaries, the capillaries running transverse to the main plane of the substrate.

This helps to reduce spreading of the supernatant in a direction parallel to the backside of the device. The compound remains more localized on the substrate, rendering it easier to detect.

According to a favourable embodiment, the backside of the device is a hydrophobic backside.

This helps to prevent the flow of liquid emanating from a through-hole sideways. The backside may for example have been provided with a hydrophobic coating, or may have been chemically treated to render it hydrophobic. If the device is a silicon-based device, it may for example be treated with tetramethyl-silane.

According to a favourable embodiment, the compound is an antibody.

This is an important field of application.

According to a favourable embodiment, the cell is selected.

The selected cell may be used for a variety of purposes, such as propagation, sequencing etc. Typically selecting the cell will involve its removal from the well.

According to a favourable embodiment, the selected cell is propagated.

Thus advantage can be taken from the properties of the cell selected using the assay.

According to a favourable embodiment, the selected cell contains a poly nucleic acid sequence and the method comprises at least one further step chosen from i) multiplication of the poly nucleic acid sequence, ii) determining the nucleotide sequence of the poly nucleic acid sequence, and iii) isolating the poly nucleic acid sequence.

Such a further step is important for valorisation of the method according to the invention.

According to a favourable embodiment, after the step of transferring the liquid to the device and before the use of the substrate for the assay the device is separated from the substrate.

Thus the substrate is removed before any reagent for the assay is added, avoiding that the cells are subjected to the reagent(s) used in the assay. It may also reduce the risk of contamination of the cells.

Transferring compound may be done during incubation of the device containing cells, or may be done by stamping the device containing cells on the substrate and the cells may be incubated further as desired.

Figure 2:
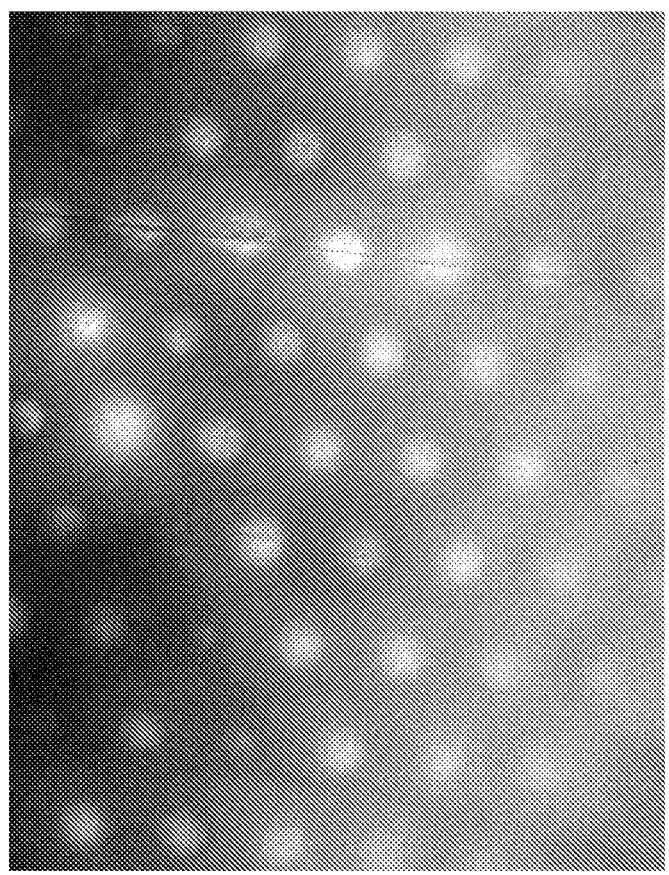
Figure 3B:
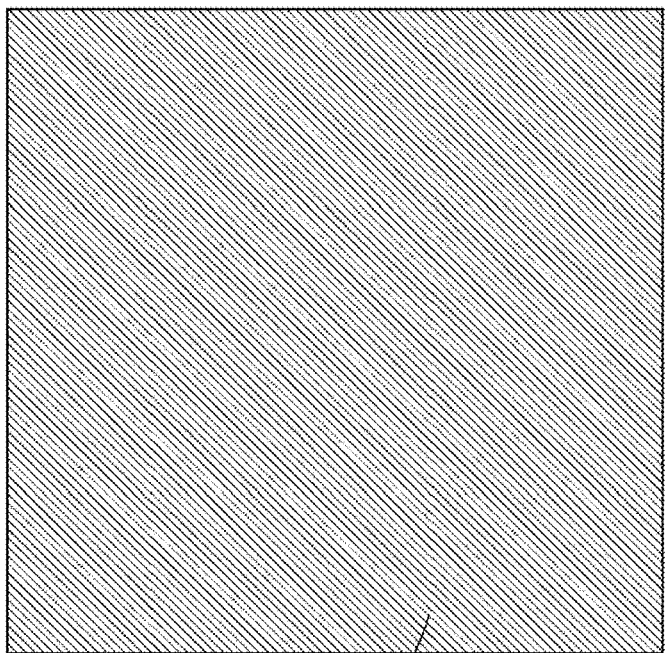
Figure 3B:
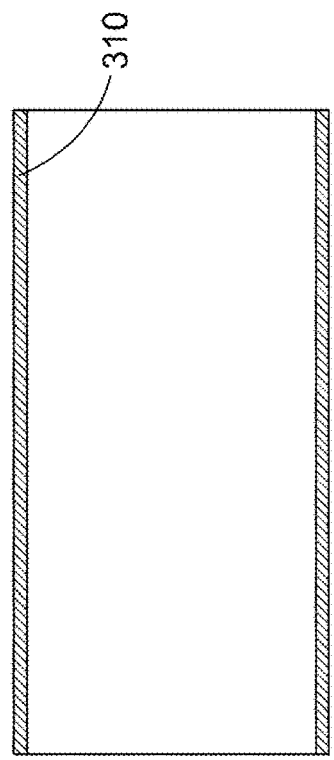
Figure 3A:
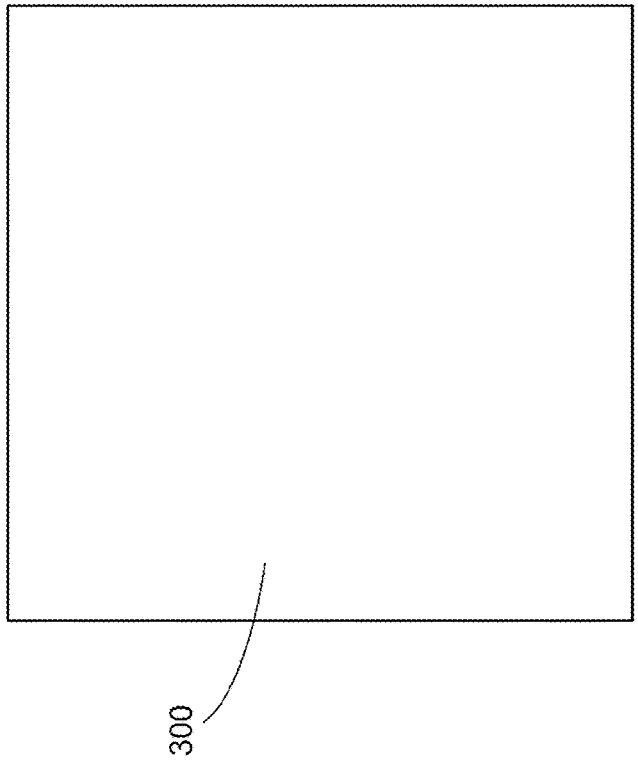
Figure 3A:
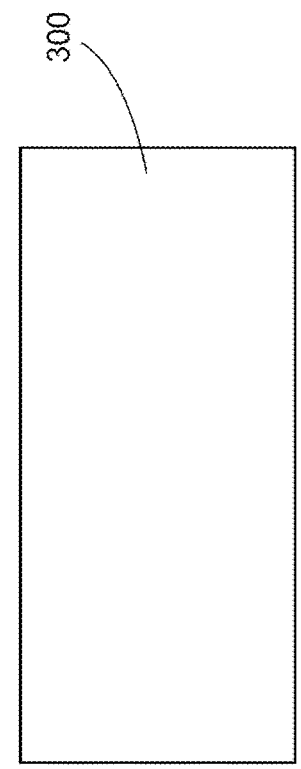
Figure 3D:
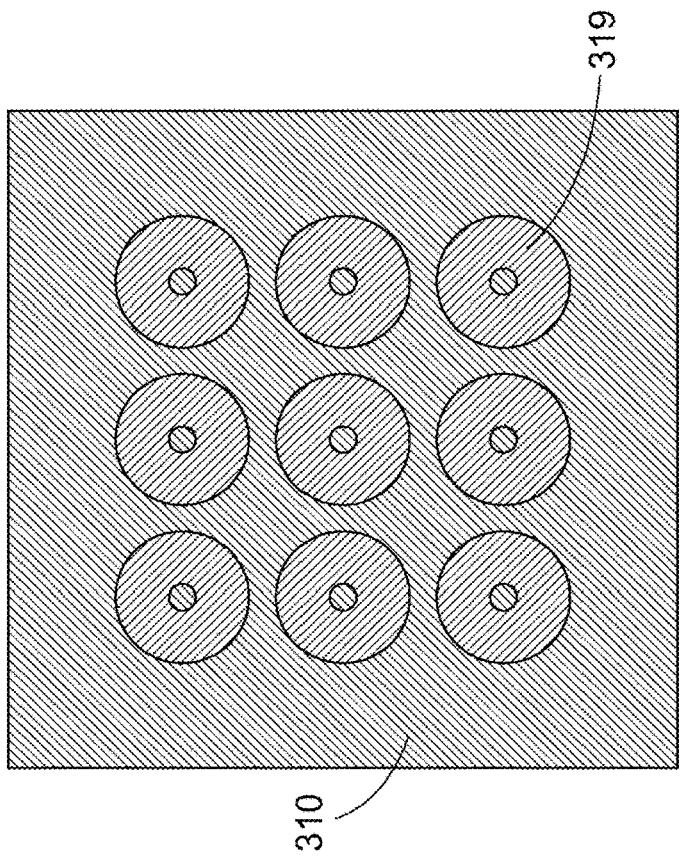
Figure 3D:
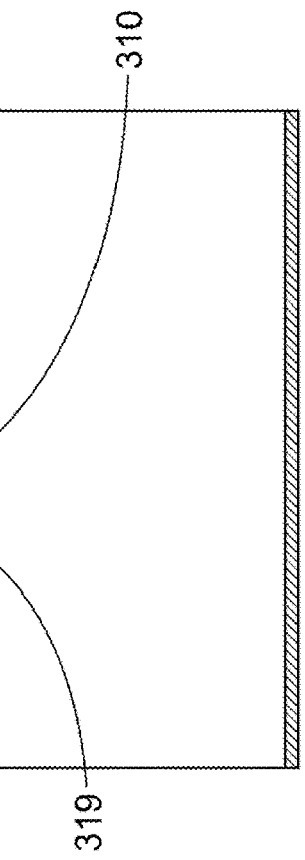
Figure 3C:
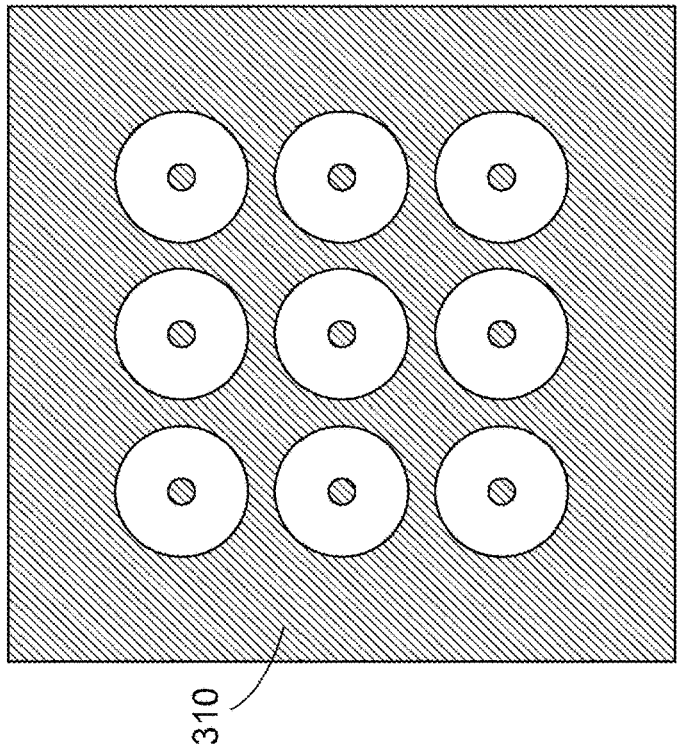
Figure 3C:
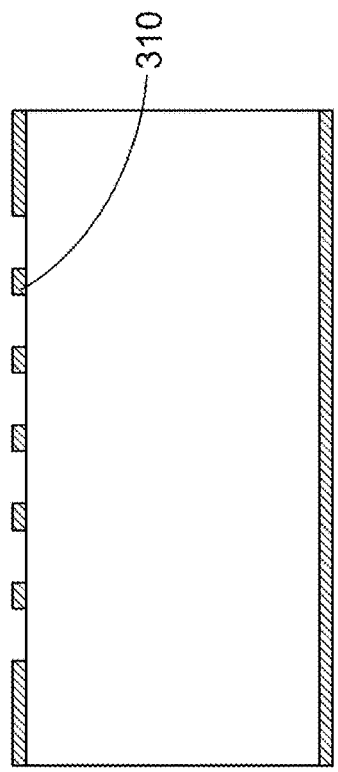
Figure 3F:
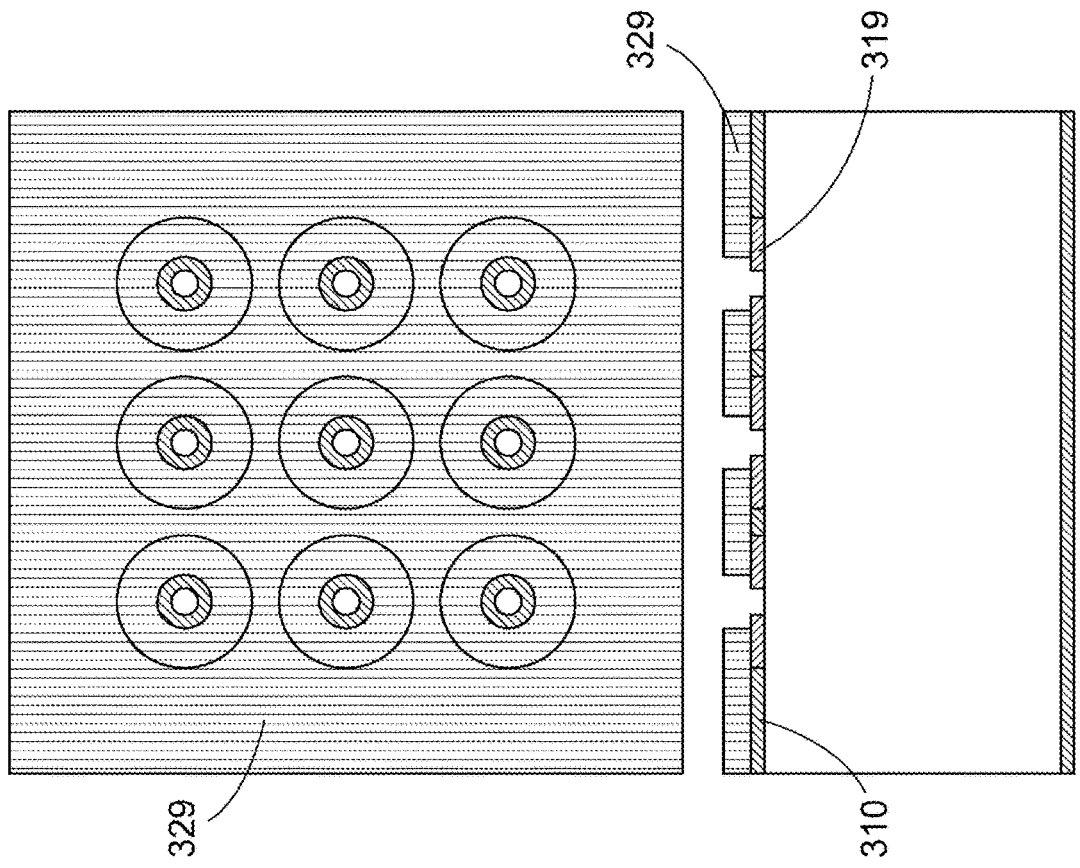
Figure 3E:
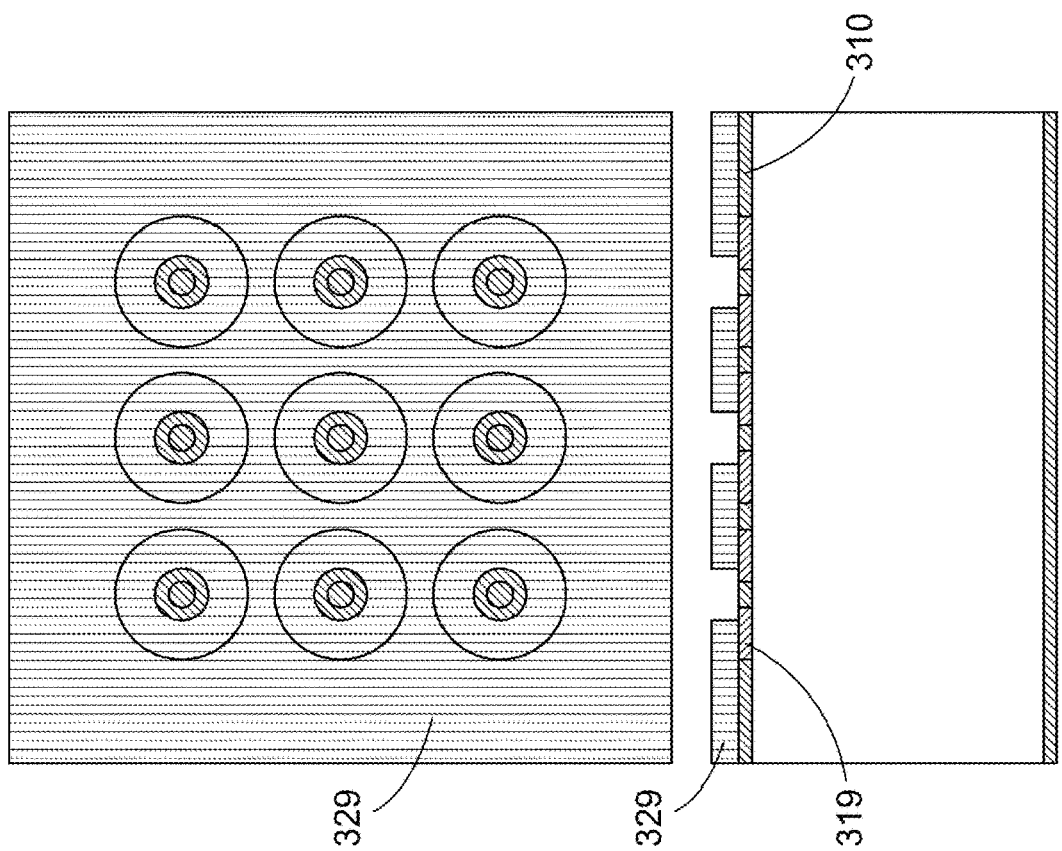
Figure 3J:
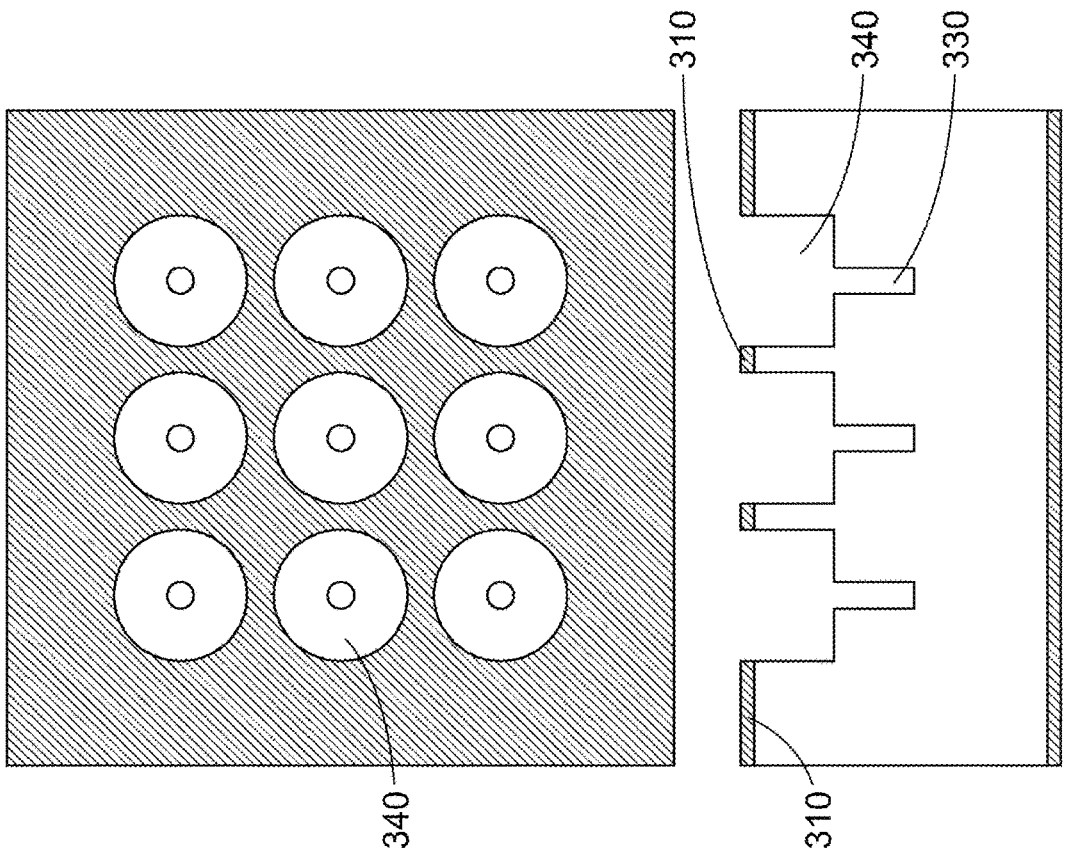
Figure 3I:
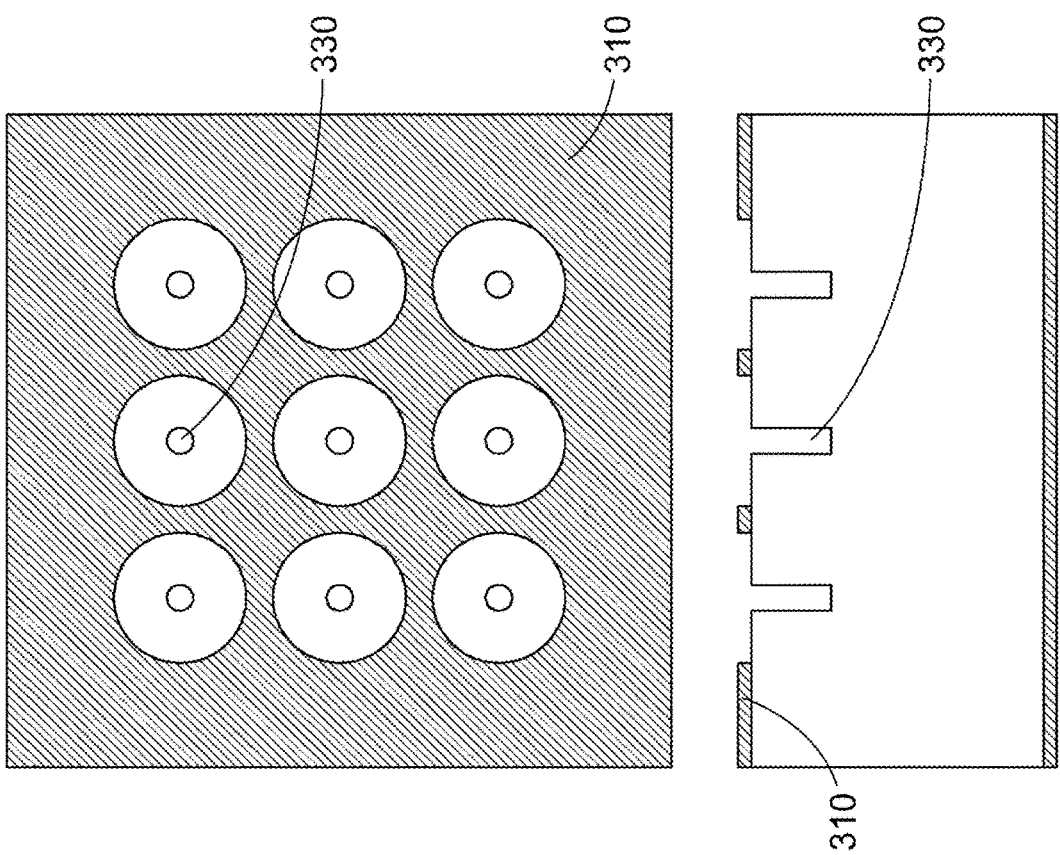
Figure 3L:
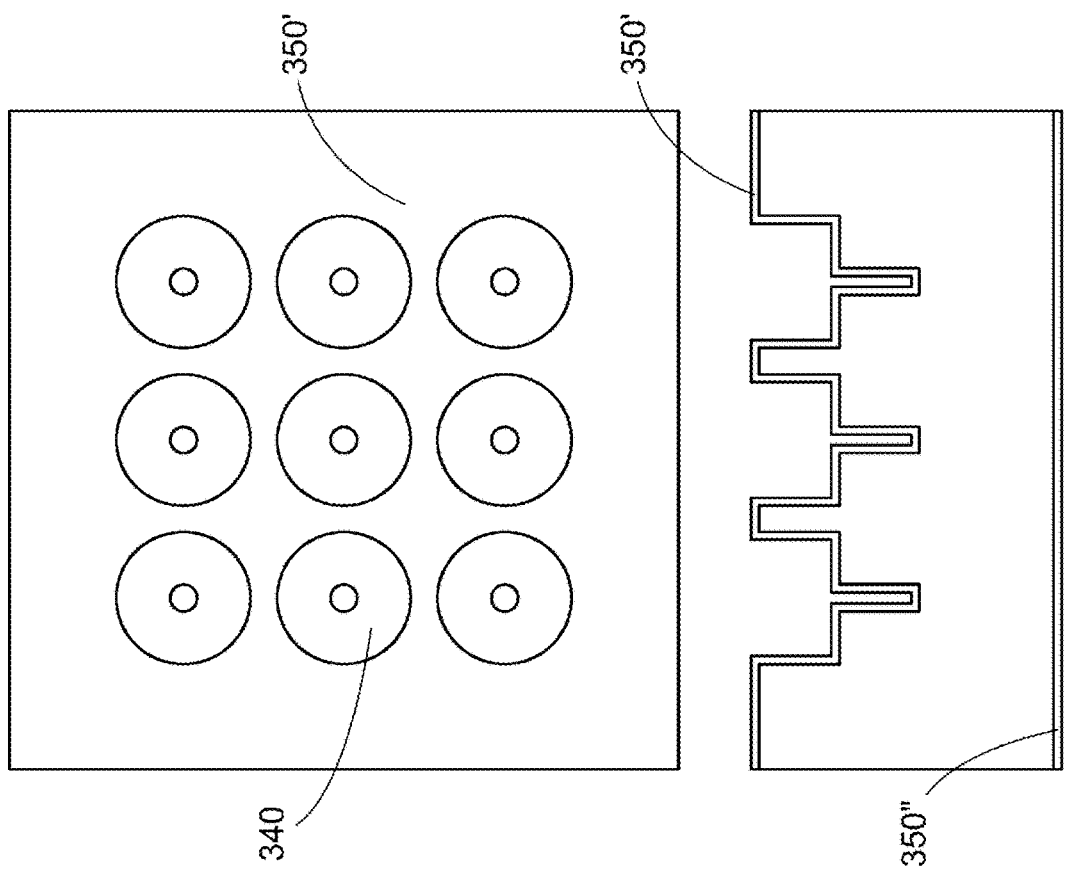
Figure 3K:
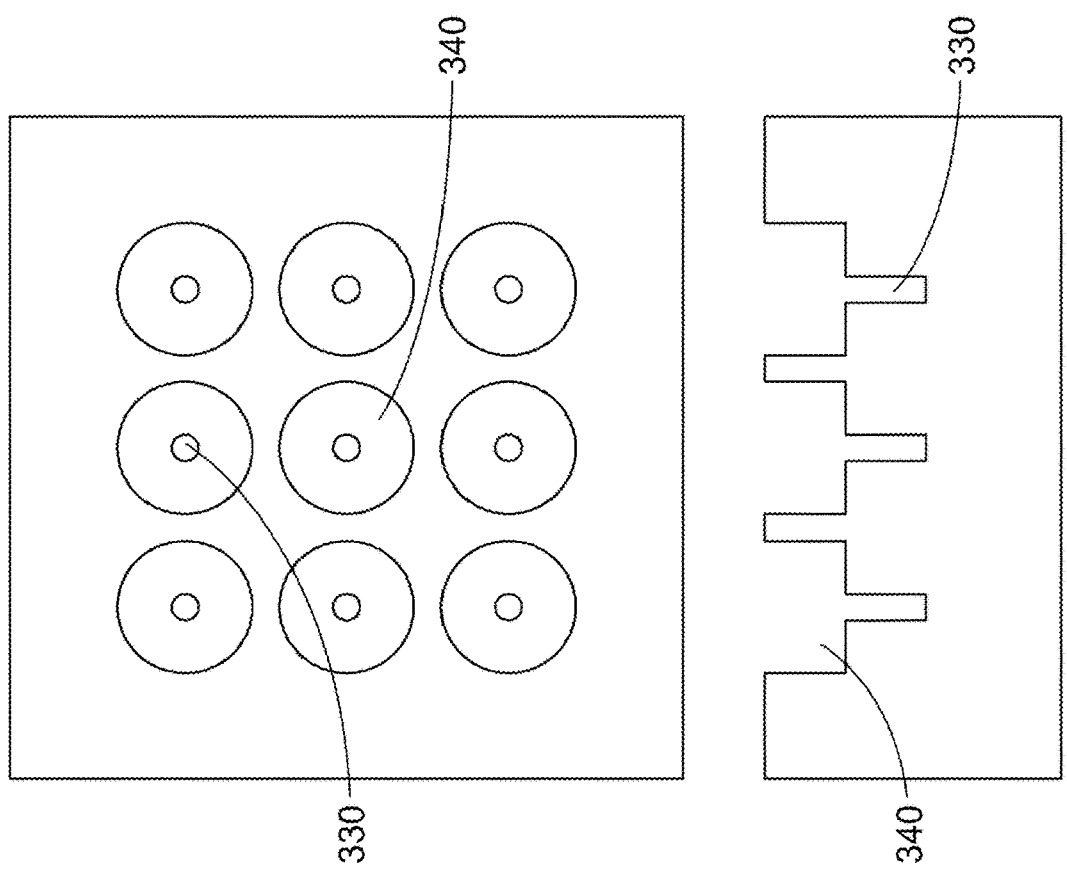
Figure 3P:
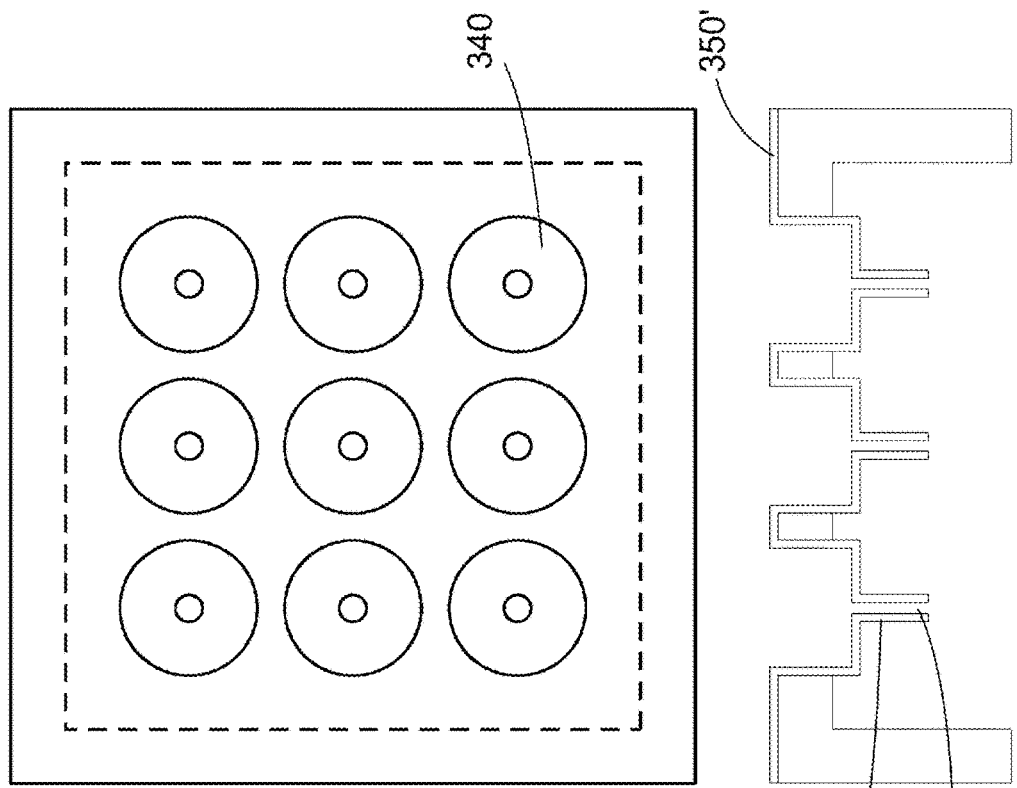
Figure 3O:
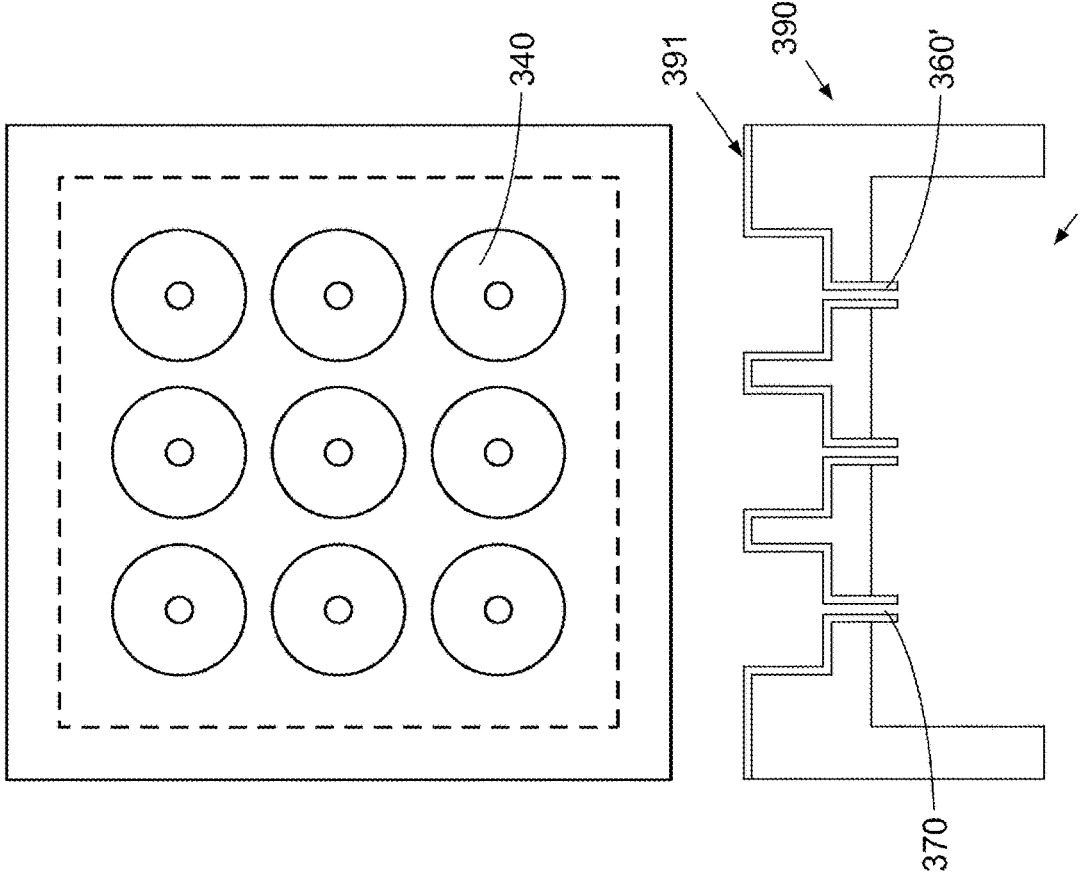

The invention will now be illustrated with reference to the example section below, and with reference to the drawing wherein FIG. 1 shows a photograph of a model experiment for estimating minimal sensitivity achievable by the method according to the invention;

FIG. 2 shows a photograph of an experiment demonstrating the feasibility of transfer of fluorescently labeled antibody from a microsieve onto a PVDF membrane; and FIG. 3A to FIG. 3O schematically shows a method of manufacturing a micro-sieve suitable for use in the present invention both in top view and cross-sectional view.

Firstly an envisaged method of manufacturing a micro-sieve 390 (FIG. 3O) suitable for use in the present invention will be described, which micro-sieve 390 has capillaries 360' (tubes) protruding from the backside of the device 390.

Single crystal silicon can used as a main structural material for the membrane.

Fabrication Steps:

FIG. 3A. The process starts with a silicon wafer 300. A {100} silicon wafer is preferential because in that case wet anisotropic etching can be used to release the membrane.

FIG. 3B. Deposition of a silicon nitride layer 310 using Low Pressure Chemical Vapor Deposition (LPCVD).

FIG. 3C. Patterning of silicon nitride 310 using Reactive Ion Etching (RIE). Here a 3×3 matrix is schematically shown, but in practice the matrix is much larger for example 100×100. The plurality of wells to be formed is not limited to a particular shape, such as rectangular, although a grid-like placement of the wells is preferred.

FIG. 3D. Local Oxidation of Silicon (LOCOS) to form a temporary silicon oxide layer 319.

FIG. 3E. Resist patterning, with resist layer 329.

FIG. 3F. Selective removal of silicon nitride using RIE.

FIG. 3G. Deep Reactive Etching of Silicon (DRIE) to form small round holes 330.

FIG. 3H. Resist removal using O$_2$-ashing and chemical cleaning with 100% HNO$_3$.

FIG. 3I. Selective removal of silicon oxide of the temporary layer 319 using wet chemical etching in hydrofluoric acid (HF) or buffered HF.

FIG. 3J. Deep Reactive Etching of Silicon (DRIE) to form cups 340 (wells 340) and at the same time to further deepen the holes 330.

FIG. 3K. Removal of the first silicon nitride layer 310 using HF or hot phosphoric acid (H$_3$PO$_4$).

FIG. 3L. Deposition of a first low stress silicon nitride layer 350' (SiRN) and second low stress silicon nitride layer 350" on the backside of the wafer 300 by LPCVD.

FIG. 3M. Patterning of the second silicon nitride layer 350" on the backside of the wafer 300 using RIE of silicon nitride.

FIG. 3N. Backside etching of silicon in order to form a silicon membrane and expose closed silicon nitride tubes 360. Note that the bottom of the cups 340 is not exposed in this step. For this step wet anisotropic etching of silicon in TMAH may be used. DRIE process could be used as well, alone or in combination with wet anisotropic etching.

FIG. 3O. RIE directional etching of silicon nitride from the backside of the wafer 300 in order to create open capillaries 360' (defining through-holes 370). This is a device 390 suitable for use in the method according to the invention, with a frontside 391 and a backside 392. The through-hole 370 of a capillary 360' connects a well 340 with the backside 392.

FIG. 3P. Backside etching to expose the bottom of the cups 340 in order to make the membrane locally optically transparent, more specifically the (thin) bottoms of the cups 340.

The invention also relates to a method of manufacturing a device using the method steps described above, with any step involving the removal of resist or a previously formed layer not being limited to the specific chemicals and/or concentrations thereof mentioned.

Example 1

Spotting Experiment for Estimating Minimal Sensitivity (Model Experiment not According to the Invention)

PVDF (Polyvinylidene difluoride) membrane (Immun-Blot® low fluorescence PVDF membrane, BioRad Laboratories B.V., Veenendaal, The Netherlands) was activated in methanol and MilliQ® purified water according to protocol manufacturer.

The PVDF membrane was placed onto filter paper (Bio-Rad, included with the purchased PVDF) wetted in PBS.

A rhEpCAM (recombinant human EpCAM protein, ACRO Biosystems, EPM-H5223, Bethesda, MD, USA) dilution series was prepared in PBS buffer:
A) 100 ng/μL
B) 10 ng/μL
C) 1 ng/μL
D) 100 pg/μL
E) 10 pg/μL
F) 1 pg/μL
G) 0 pg/μL 1 μL of each concentration was pipetted manually onto the pretreated PVDF membrane.

After 10 minutes to allow the droplets to be absorbed, the PVDF membrane with spots A)-G) was incubated with 2 mL blocking buffer (PBS, 1% BSA) for 15 minutes.

Preparation Anti-Human EpCAM FITC Solution 2.32 μL of anti-human EpCAM FITC (0.43 mg/mL from AcZon, Bologna, Italy) was pipetted into 2.32 mL PBS buffer.

The blocking buffer was removed and the PVDF membrane was incubated for 15 minutes in 2 mL anti-human EpCAM FITC solution.

The antibody solution was removed and the PVDF membrane was washed in washing buffer (PBS) for 2×5 minutes.

The PVDF strip was viewed under a fluorescence microscope. The spot diameter was 2 mm and a concentration of 1 ng/μl (C) was clearly visible (FIG. 1) while the 100 pg/μl spot was discernible with the eye.

The spot diameter in FIG. 1 is 2 mm, i.e. quite large, indicating that the read-out sensitivity for smaller spots with the same fluorescent-protein concentration is below 1 ng. If the diameter of the spots is smaller, then the sensitivity is even well below 1 ng.

Example 2

Transfer of Fluorescently Labeled Antibody from a Microsieve onto a PVDF Membrane Preparation of the Device A microsieve was de-aerated in methanol and washed with MilliQ® purified water. The microsieve was obtained from VyCap BV (Deventer, The Netherlands) and used without the plastic holder it is sold in. The microsieve has through-holes with a diameter of 5 μm.

PVDF Membrane Preparation

PVDF (Polyvinylidene difluoride) membrane (0.20 μm pore size, Immun-Blot® low fluorescence PVDF membrane, BioRad Laboratories B.V., Veenendaal, The Netherlands) was activated in methanol and MilliQ® purified water according to protocol manufacturer.

Transfer of Fluorescently Labelled Antibody to the PVDF Membrane

The microsieve without holder was placed onto a wet PVDF membrane floating on MilliQ® purified water in a Petri dish. (In another experiment, the micro sieve was placed onto filter paper (Bio-Rad, included with the purchased PVDF wetted in MilliQ® purified water) which also worked).

6 μL anti-IgG PE (Sigma-Aldrich, P8547, 0.1-0.3 μg/μL, diluted 1:20, phycoerythrin labeled) was pipetted onto the microsieve.

The microsieve was removed by lifting it vertically and the PVDF membrane was imaged under a fluorescence microscope. It was found that the solution was successfully passed through the microsieve and tiny fluorescent spots were visible. These spots had a diameter of about 40 μm.

Example 3

Assay of Single Hybridomas Cells Producing an Antibody Against an Antigen on Antigen-Coated PVDF (According to the Invention)

PVDF Membrane Preparation

Activation step: Activate the micro-porous PVDF membrane in methanol and MilliQ® purified water according to protocol manufacturer. The PVDF membrane with a pore size of 0.45 μm was Immun-Blot® low fluorescence PVDF membrane (BioRad Laboratories B.V., Veenendaal, The Netherlands).

Coating step: Apply 500 μL 10 ng/μL antigen on PVDF and incubate for 15 minutes.

Blocking step: Incubate PVDF 15 minutes in PBS, 1% BSA.

Preparation of Device

The microsieve suitable for use in these experiments can be obtained from VyCap BV (Deventer, The Netherlands) and its plastic holder will be removed for our experiments.

This microsieve will be de-aerated in methanol, washed with MilliQ® purified water in accordance with the protocol of the manufacturer and placed in PBS.

Cell Loading of the Microsieve

Hybridoma cells can be cultivated in a suitable culture medium (such as Gibco® CD hybridoma, +4 mM L-Glutamine, +1% penicillin/streptomycin). Prior to loading the microsieve with the hybridoma cells, the hybridoma cells will be washed to remove the antibody already present in the culture medium. The hybridoma cell suspension will be centrifuged at 300 rpm for 5 minutes. Excess medium will be removed and the cells will be re-suspended in fresh medium at a concentration of approximately 3000 cells in 50 µL medium. The microsieve will be loaded with cells in accordance to the instructions of the manufacturer, with the microsieve being placed on a sponge (Vycap BV). The cell suspension will be pipetted onto the microsieve and, after the cells are sufficiently loaded into the wells, the microsieve may be submerged fully in medium. Excess medium will be removed before further handling of the microsieve.

Transfer of Supernatant to the PVDF Membrane

Wet filter paper soaked in PBS will be placed in a petridish.

The antigen-coated PVDF membrane will be placed on top of said filter paper taking care that no air is trapped between the filter paper and the membrane.

The microsieve with cells will be placed on the PVDF membrane and allowed to sit overnight in an incubator at 37° C., 100% humidity, 5% $CO_2$.

Incubation with Fluorescently Labelled Anti-Antibody

After the incubation period the PVDF will be removed and rinsed with PBS (2×5 minutes) and incubated with 10 ng/µL anti-IgG-PE for 15 minutes. Anti-IgG-PE (Sigma-Aldrich Corp., St. Louis, MO, USA) contains phycoerythrin as a fluorescent label.

The PVDF membrane can be examined under a fluorescence microscope. The differences in fluorescence intensity are proportional to the antibody production levels of individual hybridomas cells.

Example 4

Assay of Single Hybridomas Cells Producing Antibody Against the Antigen on Unmodified PVDF (According to the Invention)

This experiment can be performed analogous to Example 3 except for the PVDF preparation which will not be coated with the antigen. After contacting the PVDF membrane with the liquid from the wells, the PVDF membrane is blocked, e.g. using the BSA solution and then incubated with the fluorescently labelled anti-antibody.

The PVDF membrane can be examined under a fluorescence microscope. Differences in fluorescence intensity are proportional to differences in antibody production levels of individual hybridomas cells.

Example 5

Stamping on PVDF (According to the Invention)

Experiment 3 can be continued as follows. After the overnight incubation, the microsieve of Example 3 can be placed for 5 minutes on a freshly prepared PVDF membrane coated with antigen as described in Example 3.

Visual examination under a fluorescence microscope can be used to reveal that the fluorescent spots are more localised.

The invention claimed is:

1. A method of selecting a biological cell by performing assays on a compound excreted by biological cells, the method being performed using a device, wherein the device comprises:

a frontside with a plurality of wells; and a backside wherein each respective well of the plurality of wells comprises a respective bottom provided with a respective through-hole extending from the respective well to the backside, wherein the wells of the plurality of wells contain biological cells, and wherein each respective through-hole has smaller dimensions than the biological cells in the plurality of wells and thereby physically retains the biological cells in the wells, wherein at least 10% of the plurality of wells contain only a single biological cell;

wherein said method comprises:

contacting the backside of the device with a substrate such that a substantially respective straight passage from each respective through-hole to the substrate is established wherein each respective straight passage is substantially coaxial with each respective through-hole and is substantially perpendicular to the backside, wherein the biological cells excrete a compound in the plurality of wells and following excretion of the compound by the cells in the plurality of wells, the method further comprises:

transferring a liquid from the plurality of wells via the through-holes to the substrate;

performing a first assay using the substrate; and selecting a biological cell from a well of the plurality of wells, wherein the device is held in a position with the backside oriented substantially downward between the transferring of the liquid from the plurality of wells to the substrate via the through-holes and performing the first assay using the substrate.

2. The method according to claim 1, wherein the first assay is an immunoassay.

3. The method according to claim 1, wherein the substrate comprises a micro-porous substrate.

4. The method according to claim 3, comprising transferring the liquid using a pressure difference wherein a pressure at a side of the substrate facing opposite from the backside of the device is lower than a pressure at a side of the substrate facing the backside of the device.

5. The method according to claim 1, wherein the substrate is a polymer.

6. The method according to claim 1, wherein the backside comprises a plurality of protruding capillaries, the capillaries running in a direction transverse to a main plane of the substrate and through the device from the frontside to the backside.

7. The method according to claim 1, wherein the backside of the device is a hydrophobic backside.

8. The method according to claim 1, wherein the compound is an antibody.

9. The method according to claim 1, further comprising propagating the selected biological cell.

10. The method according to claim 1, wherein the selected biological cell contains a poly nucleic acid sequence and the method further comprises at least one further step chosen from i) multiplying the poly nucleic acid sequence, ii) sequencing the poly nucleic acid sequence, and iii) isolating the poly nucleic acid sequence.

11. The method according to claim 1, further comprising separating the device from the substrate after transferring the liquid to the device and before performing the first assay using the substrate.

12. The method of claim 5, wherein the polymer is chosen from i) polyvinylidene difluoride, and ii) nitrocellulose.

13. The method of claim 1, further comprising retaining the selected biological cell in the well for performing a second assay.

14. The method of claim 1, further comprising keeping the selected biological cell physically from the substrate.

15. The method of claim 1, wherein each through-hole is adapted to transfer liquid containing the compound to a spot of a size smaller than a surface area of the well in a main plane of the device.

16. The method of claim 15, wherein the backside comprises a plurality of protruding capillaries, the capillaries running in a direction transverse to a main plane of the substrate and through the device from the frontside to the backside wherein the capillaries define the through-holes.

* * * * *